US010828177B2

(12) United States Patent
Strbac et al.

(10) Patent No.: US 10,828,177 B2
(45) Date of Patent: Nov. 10, 2020

(54) SYSTEM AND METHOD FOR ELECTROTACTILE FEEDBACK

(71) Applicant: FUNDACIÓN TECNALIA RESEARCH & INNOVATION, San Sebastián-Guipúzcoa (ES)

(72) Inventors: Matija Strbac, San Sebastián-Guipúzcoa (ES); Goran Bijelíc, San Sebastián-Guipúzcoa (ES); Nebojša Malesevic, San Sebastián-Guipúzcoa (ES); Thierry Keller, San Sebastián-Guipúzcoa (ES)

(73) Assignee: FUNDACIÓN TECNALIA RESEARCH & INNOVATION, Guipúzcoa (ES)

( * ) Notice: Subject to any disclaimer, the term of this patent is extended or adjusted under 35 U.S.C. 154(b) by 135 days.

(21) Appl. No.: 15/536,570

(22) PCT Filed: Dec. 18, 2015

(86) PCT No.: PCT/EP2015/080677
§ 371 (c)(1),
(2) Date: Jun. 15, 2017

(87) PCT Pub. No.: WO2016/097382
PCT Pub. Date: Jun. 23, 2016

(65) Prior Publication Data
US 2017/0348117 A1    Dec. 7, 2017

(30) Foreign Application Priority Data

Dec. 19, 2014  (EP) ..................................... 14382549

(51) Int. Cl.
*A61F 2/68*     (2006.01)
*A61F 2/58*     (2006.01)
(Continued)

(52) U.S. Cl.
CPC ................ *A61F 2/68* (2013.01); *A61F 2/583* (2013.01); *A61F 2/60* (2013.01); *A61F 2/72* (2013.01);
(Continued)

(58) Field of Classification Search
CPC .... A61F 2/583; A61F 2/68; A61F 2002/5058; A61F 2002/6827; A61B 5/7455
See application file for complete search history.

(56) References Cited

U.S. PATENT DOCUMENTS 4,808,187 A *  2/1989  Patterson .................. A61F 2/72
                                                          623/25
6,500,210 B1 * 12/2002 Sabolich ................. A61F 2/583
                                                          623/24
(Continued)

FOREIGN PATENT DOCUMENTS

WO        9825552 A1     6/1998
WO        9848740 A1    11/1998
(Continued)

OTHER PUBLICATIONS

Microchip. PC16F877 microcontroller. (Year: 2019).*
(Continued)

*Primary Examiner* — Christie L Bahena
(74) *Attorney, Agent, or Firm* — Cantor Colburn LLP

(57) ABSTRACT

A system and method for transferring proprioceptive and/or sensory information from a prosthesis or from a sensing system disposed at a body part having poor or no sensation, to the skin of a user wearing the prosthesis or the sensing system, includes: a device for providing electrotactile feedback in the form of an electrical stimulation pattern with coding scheme for at least one input signal; and at least one multi-pad electrode configured to be positioned on a part of the body of the user. The multi-pad electrode includes a (Continued)

plurality of pads configured to be selectively and discretely activated/deactivated according to the predefined stimulation pattern.

20 Claims, 7 Drawing Sheets

(51) Int. Cl.
    *A61F 2/60* (2006.01)
    *A61F 2/80* (2006.01)
    *A61F 2/72* (2006.01)
    *A61F 2/50* (2006.01)
    *A61F 2/76* (2006.01)

(52) U.S. Cl.
    CPC ........ *A61F 2/80* (2013.01); *A61F 2002/5058* (2013.01); *A61F 2002/6827* (2013.01); *A61F 2002/762* (2013.01); *A61F 2002/7625* (2013.01); *A61F 2002/7635* (2013.01)

(56) References Cited

U.S. PATENT DOCUMENTS

| | | | |
|---|---|---|---|
| 8,974,402 B2* | 3/2015 | Oddsson | A61B 5/1038 600/595 |
| 2009/0048539 A1 | 2/2009 | Lundborg | |
| 2012/0065743 A1* | 3/2012 | Gill | A61F 2/583 623/57 |

FOREIGN PATENT DOCUMENTS

| | | |
|---|---|---|
| WO | 03086235 A2 | 10/2003 |
| WO | 2006101445 A1 | 9/2006 |
| WO | 2012055029 A1 | 5/2012 |

OTHER PUBLICATIONS

Andrew Y. J. Szeto et al., "Electrocutaneous Stimulation for Sensory Communication in Rehabilitation Engineering", IEEE Transactions on Biomedical Engineering, Apr. 1982, vol. BME-29, No. 4, pp. 300-308.
Bo Geng et al, "Impacts of selected stimulation patterns on the perception threshold in electrocutaneous stimulation", Journal of NeuroEngineering and Rehabilitation 2011, vol. 8, No. 9, pp. 1-10.
C. Antfolk et al., "Sensory feedback in upper limb prosthetics", Hand Clinics, 2001, vol. 17, No. 3, pp. 1-23.
Christian Cipriani et al., "A Miniature Vibrotactile Sensory Substitution Device for Multifingered Hand Prosthetics", IEEE Transactions on Biomedical Engineering, Feb. 2012, vol. 59, No. 2, pp. 400-408.
Fredrik C. P. Sebelius et al., "Refined Myoelectric Control in Below-Elbow Amputees Using Artificial Neural Networks and a Data Glove", The Journal of Hand Surgery, vol. 30, Issue 4, Jul. 2005, pp. 780-789.
Heidi J. B. Witteveen et al. "Grasping Force and Slip Feedback through Vibrotactile Stimulation to be Used in Myoelectric Forearm Prostheses", 34th Annual International Conference of the IEEE EMBS, San Diego, California USA, Aug. 28-Sep. 1, 2012, pp. 2969-2972.
R. R. Riso, "Strategies for providing upper extremity amputees with tactile and hand position feedback—moving closer to the bionic ar", Technology and Health Care, IOS Press, 1999, vol. 7, No. 6, pp. 401-409.
Robert W. Mann et al. "Kinesthetic Sensing for the EMG Controlled ""Boston Arm", IEEE Transactions on Man-Machine Systems, Mar. 1970, vol. 11, No. 1, pp. 110-115.
Heidi J. B. Witteveen et al., Vibro- and Elecrotactile User Feedback on Hand Opening for Myoelectric Forearm Prostheses; IEEE Transactions on Biomedical Engineering, Aug. 1, 2012; vol. 59, No. 8, pp. 2219-2226.
International Search Report dated Mar. 24, 2016 re: Application No. PCT/EP2015/080677; pp. 1-4; citing: WO 03/086235 A2, WO 98/25552 A1, WO 2012/055029 A1, WO 2006/101445 A1, and Witteveen et al.
Written Opinion dated Mar. 24, 2016 re: Application No. PCT/EP2015/080677; pp. 1-6; citing: WO 03/086235 A2, WO 98/25552 A1, WO 2012/055029 A1, WO 2006/101445 A1.

\* cited by examiner

SYSTEM AND METHOD FOR ELECTROTACTILE FEEDBACK

TECHNICAL FIELD

The present disclosure relates to the field of prosthesis, such as hand prosthesis, or to body parts without sensation and, in particular, to electrical stimulation devices that provide electrotactile feedback for such prosthesis or body parts without sensation.

BACKGROUND

Multifunctional motorized prostheses capable of opening or closing the hand on the basis of Electromyography (EMG) control signals (myoelectric prostheses) that are available on the market are currently facing several challenges. They usually allow only two degrees of freedom (hand opening and closure), they lack sensory feedback, they have limited battery lifetime and are rather of excessive weight and accumulate heat during whole day carrying. Such drawbacks result in an average rejection rate of myoelectric prostheses that is today more than 25%. Ongoing research, including the combined use of multiple EMG recordings and artificial neural networks may soon form a base for neural control of more advanced hand prostheses, providing a large number of degrees of freedom as described by F. C. P. Sebelius et al. in "Refined Myoelectric Control in Below-Elbow Amputees Using Artificial Neural Networks and a Data Glove", The Journal of Hand Surgery, Volume 30, Issue 4, July 2005, pages 780-789.

However, the lack of sensory feedback that will enable the user to identify the artificial hand as "a part of his/her body" still represents a fundamental problem. A hand without sensory functions is perceived as a foreign body and is often denied by the owner, as stated by Ramachandran and Blakeslee in 1998. The proprioceptive information and the sense of touch, that can enable regulation of grip force and execution of delicate motor tasks, are essential for the user to identify with the artificial hand.

Several sensory feedback interfaces in hand prostheses have been tested over the years and reported for example by R. R. Riso in "Strategies for providing upper extremity amputees with tactile and hand position feedback—moving closer to the bionic arm", Technology and Health Care, IOS Press, Volume 7, Number 6/1999, pages 401-409 and by G. Lundborg and B. Rosén in "Sensory substitution in prosthetics, Hand Clinics, 2001, 17(3):481-8.

We recognize three approaches for providing sensory feedback to the user:

The first one is based on the use of an intact sensory system to replace the missing one. This method is automatically used by amputees using myoelectric prostheses that utilize vision to guide the movements of the prosthetic hand. The use of hearing as substitution for missing sensation has been described as an effective strategy in major nerve injuries leaving the hand void of sensation and has also been tried in hand prostheses, as described in international patent application WO9848740.

The second one is based on direct stimulation of intact nerves. Various types of nerve interfaces have been used in laboratory environment (Riso, 1999). The theoretical advantage of the nerve-interface strategies is that sensory stimuli can be directly transferred into peripheral nerves and can thereby reach the Central Nervous System (CNS). However, there are several drawbacks and difficulties. A transcutaneous passage device or telemetric techniques are required to transfer the sensory information from the outside of the body to the inside. The electric stimulation of sensory fascicles may not be modality-specific and may give rise to non-physiological and weird sensory perception. Direct stimulation of intact nerves principle will therefore remain on the experimental stage for many years to come.

The third approach is based on stimulation of intact skin cutaneous receptors in a remote area of the body. Attempts to use transferred cutaneous stimulation to remote skin areas were already tried several decades ago. According to this principle remote skin areas of the body can be subjected to electro-cutaneous stimulation (as stated by Szeto and Riso in chapter 3 of the book "Rehabilitation Engineering", ISMB 0-8493-6951-7, 1990) or vibration (as stated by Mann and Reimers in "Kinesthetic sensing for the EMG controlled "Boston Arm"", IEEE Trans. Man Mach. Syst., 11(1), 110, 1970). The early prototypes showed that the closed loop can be implemented, but that the simple interfaces (e.g., single channel stimulation) have limited applicability because of very unpleasant and non-physiological sensations (reported by Lundborg et al., 1999). New complex feedback interfaces that will enable more intuitive closed loop control are addressed in recent years. Some research groups are giving precedence to vibrotactile stimulation for sensory feedback (for example Witeveen et al in Grasping force and slip feedback through vibrotactile stimulation to be used in myoelectric forearm prostheses, Engineering in Medicine and Biology Society (EMBC), 2012 Annual International Conference of the IEEE, Page(s): 2969-2972; and Cipriani et al in A Miniature Vibrotactile Sensory Substitution Device for Multifingered Hand Prosthetics, IEEE Transactions on Biomedical Engineering (Volume: 59, Issue: 2), Page(s): 400-408, 2002). Some others are opting for electrocutaneous stimulation (such as Geng et al, in Impacts of selected stimulation patterns on the perception threshold in electro-cutaneous stimulation, Journal of NeuroEngineering and Rehabilitation 2011, 8:9; or Szeto et al. in Electrocutaneous Stimulation For Sensory Communication In Rehabilitation Engineering, Biomedical Engineering, IEEE Transactions on, BME-29 300, 1982).

United States patent application US2009/0048539A1 discloses a system for sensory feedback for a body extremity without sensation or a body extremity prosthesis. The disclosed system is formed by sensors applied to a prosthesis or to a body extremity without sensation, which are connected to a processor which collects signals from the sensors and processes them into output signals. The output signals are then transferred to a tactile display formed by signal transducers disposed on the skin of an intact neighboring body extremity of the patient. Since the naturally occurring nervous components are difficult to locate and therefore the signal transducers may not be placed in an optimal arrangement, the patient can learn how to discriminate between different stimuli with the help of hearing or vision, for example by observing which finger is exposed to a stimulus (for example heat). However, this disclosure relies on the existence of at least one sensor, arranged on a body extremity without sensation or on a body extremity prosthesis, in order to achieve functionality. This system can only be used for closed-loop control and cannot be used in feed forward setups, when feedback is coupled with control signals, such as EMG control in myoelectric prostheses.

International patent application WO98/25552 discloses an apparatus and method for providing sensory perceptions in a sensory system of a prosthetic device. Feedback is based on a direct mapping of the sensory output to a designated channel with an adequate stimulus magnitude.

International patent application WO2012/055029 discloses a display mounted on a patient (for example, on the lower back of the patient) for receiving information from a stimulation pad, for providing feedback to the user.

In sum, it is evident that there is a strong motivation in the field of prosthetics to provide applicable solutions for sensory feedback systems coupled to effective powered multifunctional prosthetic body extremities, which lead to greater acceptance and usability of prosthetic devices.

SUMMARY

The present disclosure applies the approach based on electrocutaneous stimulation over multi-pad electrodes, providing a sensory feedback interface system for body extremities prosthesis, such as hand prosthesis, or for body extremities without sensation, such as hands without sensation, which overcomes the limitations of conventional devices. In particular, the system addresses the problem of identifying with the artificial body part or body extremity (prosthetic body extremity) or with the body extremity with partial or complete loss of sensation, by providing the proprioceptive information. The sense of touch can also be provided. The information of interest is conveyed to the user's skin via electrocutaneous stimulation. This enables regulation of grip force and execution of delicate motor tasks. The device uses an intuitive and easy to learn feedback interface that can provide the user proprioceptive and sensory information from the artificial body extremity (or a sensing system for restoring the sensations to a body extremity) and enables regulation of grasping force and execution of delicate motor tasks based on changes of the multi-pad electrode configuration and the stimulation frequency. Electrode configuration changes are possible via a specially designed electrical stimulator that enables time and space distributed stimulation over the multi-pad electrode through a multiplexing unit.

Furthermore, this disclosure is also related to the protocol for coding the proprioceptive and sensory information from the artificial body extremity (or body extremity with partial or complete loss of sensation) using the location of the stimuli (active pad on the array electrode) and sets of stimulation parameters (pulse width, stimulation amplitude and frequency of stimulation) variations that encode sets of intuitive (easy to perceive and understand) feedback information/message schemes. This protocol defines an intuitive coding scheme for every set of proprioceptive or sensory information used for the control of the prosthesis or a body extremity without sensation. For instance, rotation of artificial hand is coded with rotation of active electrodes and increase of the force applied by the artificial hand is coded with the increase of stimulation frequency on the active electrodes.

According to an aspect of the present disclosure, there is provided a system for transferring proprioceptive information from a prosthesis or from a sensory system disposed at a body part having poor or no sensation, to the skin of a user wearing such prosthesis or sensory system. The system comprises: a device for providing electrotactile feedback in the form of a stimulation pattern defined from at least one input signal; and at least one multi-pad electrode configured to be positioned on a part of the body of said user, said multi-pad electrode comprising a plurality of pads configured to be selectively and discretely activated/deactivated according to said stimulation pattern.

The device comprises: means for processing said at least one input signal, wherein said at least one input signal comprises a control signal from said prosthesis or from said sensory system, thus coding said at least one input signal into one of a plurality of predefined stimulation patterns representing a corresponding plurality of operational parameters of said artificial prosthesis or sensory system; stimulating means for producing a plurality of electrical pulses based on said selected stimulation pattern; means for conducting said electrical pulses from said stimulating means to said at least one multi-pad electrode, thus selectively activating/deactivating the discrete pads of said multi-pad electrode and changing the configuration parameters of said discrete pads based on said stimulation pattern, thus enabling time and space distributed cutaneous stimulation corresponding to said at least one input signal.

In a particular embodiment, the system further comprises data acquisition means configured to capture a control signal to be provided to said processing means to be treated as input signal.

The system can be incorporated in a socket configured to be placed at one end on a stump of a body part and to receive an artificial extremity prosthesis at the opposite end. Alternatively, at least said multi-pad electrode is incorporated in a garment configured to be positioned either on a body part of a user having an artificial extremity prosthesis or on a body part of a user having a sensory system at a body extremity without sensation.

In a particular embodiment, the at least one multi-pad electrode is designed to circularly surround the stump or body part of the user, wherein the plurality of pads comprised in said at least one multi-pad electrode are disposed in single array along the multi-pad electrode.

In a preferred embodiment, the at least one input comprises at least one of control signal for the aperture, flexion, rotation and/or grasping force of a prosthesis or from a sensory system disposed at a body part having poor or no sensation. In a particular embodiment, at least one input further comprises sensory information.

In a particular embodiment, the prosthesis is an artificial hand or the body part having poor or no sensation is a hand.

Preferably, the predefined stimulation pattern is defined by some or all of the following stimulation parameters: location(s) of the activated pad(s) in the multi-pad electrode, stimulation frequency, stimulation pulse width and stimulation pulse amplitude.

Alternatively, the stimulation pattern is defined by only the following stimulation parameters: stimuli location and frequency of stimulation.

The system may be additionally configured for transferring sensory information from said prosthesis or from said sensory system disposed at a body part having poor or no sensation, to the skin of a user wearing such prosthesis or sensory system.

In another aspect of the disclosure, a method is provided, for transferring proprioceptive information from a prosthesis or from a sensory system disposed at a body part having poor or no sensation, to the skin of a user wearing such prosthesis or sensory system. The method comprises the steps of: providing electrotactile feedback in the form of a stimulation pattern defined from at least one input signal; and selectively and discretely activating/deactivating a plurality of pads of at least one multi-pad electrode positioned on a part of the body of said user, said activation/deactivation being done according to said stimulation pattern.

The step of providing electrotactile feedback in the form of a stimulation pattern defined from at least one input signal preferably comprises: processing said at least one input signal, wherein said at least one input signal comprises a control signal obtained from said prosthesis or from said sensory system, thus coding said at least one input signal into one of a plurality of predefined stimulation patterns representing a corresponding plurality of operational parameters of said prosthesis or sensory system; producing a plurality of electrical pulses based on said selected stimulation pattern comprised in a predefined mapping scheme; conducting said electrical pulses to said at least one multi-pad electrode, thus selectively activating/deactivating the discrete pads of said multi-pad electrode and changing the configuration parameters of said discrete pads based on said stimulation pattern comprised in a predefined mapping scheme, thus enabling time and space distributed cutaneous stimulation corresponding to said at least one input signal.

In a particular embodiment, the at least one input further comprises sensory information.

In a particular embodiment, the aperture of an artificial hand or of a sensory system disposed at a hand having poor or no sensation is coded as follows: in an initial position (open hand) activated pads are the two ones disposed at the furthermost dorsal part of the arm, and when the hand starts closing these pads are deactivated while adjacent pads are activated, this process being continued until the hand is closed and the pads disposed at the central volar part of the arm are activated; or vice versa, meaning that the first pads to be activated are the two ones disposed at the volar part of the arm.

In a particular embodiment, the grasping force applied by an artificial hand or measured by a sensory system disposed at a hand having poor or no sensation is coded by changing the stimulation frequency on the one or more active pads in response to changes in measured force.

In a particular embodiment, the rotation of an artificial hand or of a sensory system disposed at a hand having poor or no sensation is coded into a rotational evolution of the active pads on the multi-pad electrode, the first pad being activated corresponding to the original position of the artificial hand or sensing system at the instant of starting the rotation, while during the rotation of the artificial hand or sensing system, the already active pad being deactivated while the following pad in the direction of the rotation is activated, and so on, until the pad corresponding to the end of the rotation is activated.

In a particular embodiment, the flexion/extension of an artificial hand or of a sensory system disposed at a hand having poor or no sensation is coded into the activation of at least one additional pad on the multi-pad electrode in the preprogrammed time sequence.

In a particular embodiment, the method enables a user to simultaneously detect at least two of the following inputs:
the aperture/grasping of an artificial hand or of a sensory system disposed at a hand having poor or no sensation;
the grasping force applied by an artificial hand or measured by a sensory system disposed at a hand having poor or no sensation;
the rotation of an artificial hand or of a sensory system disposed at a hand having poor or no sensation; and
the flexion/extension of an artificial hand or of a sensory system disposed at a hand having poor or no sensation.

In a final aspect of the disclosure, it is provided a computer program product comprising computer program instructions/code for performing the method already described.

In sum, a specific solution for electrotactile feedback and a specific coding scheme of information needed to control an artificial extremity (or body extremity without sensation) is provided. In this solution, the feedback is intended to be used for intuitive control of the prosthesis and not directly to transfer the sensory data.

Additional advantages and features of the disclosure will become apparent from the detail description that follows and will be particularly pointed out in the appended claims.

BRIEF DESCRIPTION OF THE DRAWINGS

To complete the description and in order to provide for a better understanding of the disclosure, a set of drawings is provided. Said drawings form an integral part of the description and illustrate an embodiment of the disclosure, which should not be interpreted as restricting the scope of the disclosure, but just as an example of how the disclosure can be carried out. The drawings comprise the following figures.

DETAILED DESCRIPTION OF THE DRAWINGS

In this text, the term "comprises" and its derivations (such as "comprising", etc.) should not be understood in an excluding sense, that is, these terms should not be interpreted as excluding the possibility that what is described and defined may include further elements, steps, etc.

In the context of the present disclosure, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially".

The term "body extremity" of "body part" is intended along this text to refer to an arm or a leg or a part thereof (for example one or more fingers or toes or parts thereof), or a whole hand or foot or a part thereof, a forearm or a lower leg, such as the calf, or a part thereof, or the upper arm or the thigh or a part thereof.

In this text, the expressions "with no or poor sensitivity" or "without sensation" are used to refer to body parts or body extremities which, for any reason, lack sensation or have reduced sensation. Non-limiting examples of reasons for such lack of sensation are nerve injury, metabolic neuropathy and the use of neuroprostheses, i.e. systems that use electrical stimulation to actuate paralysed limbs or body parts. On the contrary, the expressions "non-damaged", "intact", "with full sensitivity" or "with full sensation" refer to body parts which, while being next to or close by body parts without sensation, have undamaged or substantially or partially undamaged tissue. When there has been an amputation of a body extremity, the non-damaged part closed to the amputated part is called "stump".

The following description is not to be taken in a limiting sense but is given solely for the purpose of describing the broad principles of the disclosure. Next embodiments of the disclosure will be described by way of example, with reference to the above-mentioned drawings showing apparatuses and results according to the disclosure.

Figure 1:
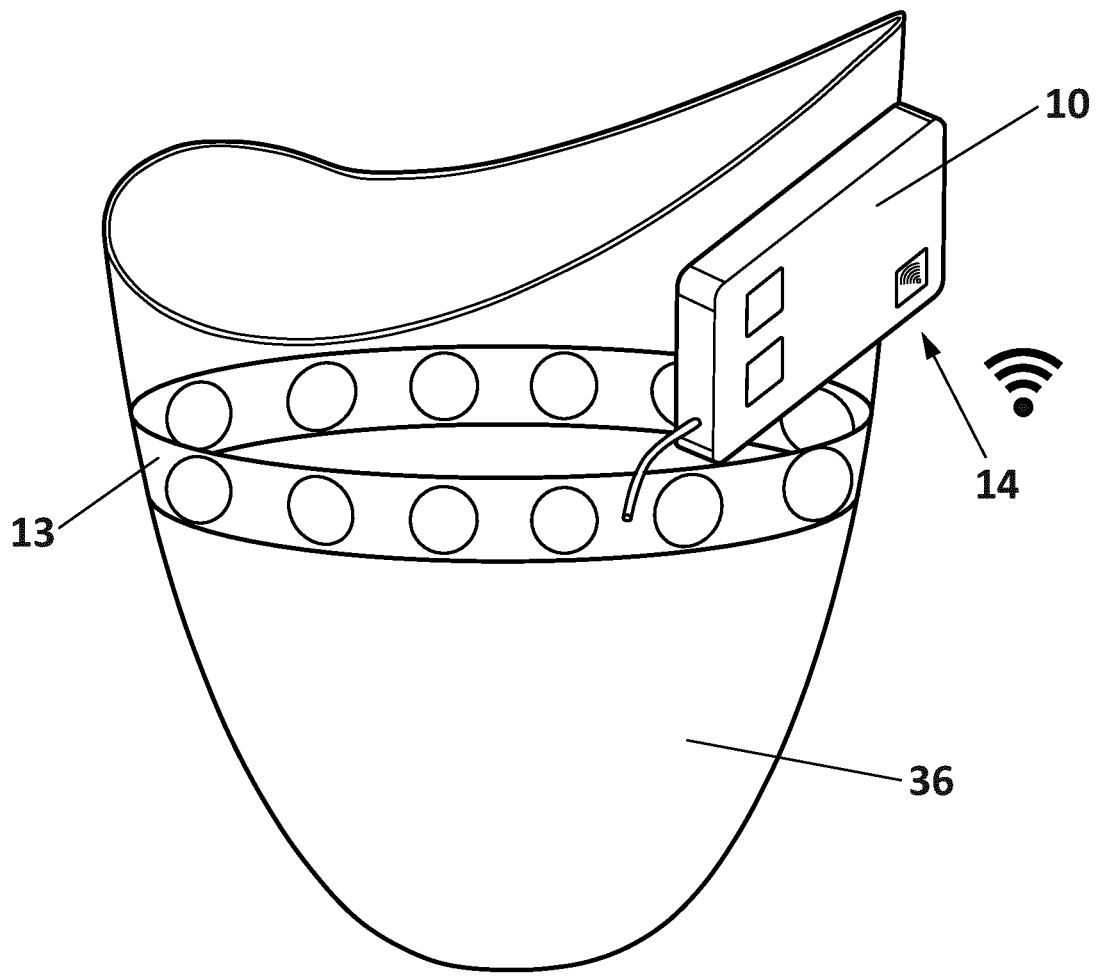
FIG. 1 shows an electrotactile feedback interface device and multipad electrode for transferring proprioceptive information from an artificial hand to the skin of the subject according to a possible embodiment of the disclosure inside the socket of a prosthesis.

FIG. 1 shows a sketch of a system for feeding back proprioceptive information from an artificial (prosthetic) body part or from a body part with partial or complete loss of sensation (not illustrated), to the skin of the subject. The system enables the user to mentally perceive natural sensation in the artificial body part or in the body part with poor or no sensation, thanks to an electrical stimulator and a multi-pad electrode which manage to stimulate the skin of a non-damaged body part (for example the forearm if the hand is missing or the upper arm if the forearm is missing). The system is based on the controlled electrical stimulation of portions of the somatosensory system. In a preferred embodiment, the controlled electrical stimulation is asynchronous and is achieved by means of a single channel stimulator and a multi-pad electrode.

As shown in FIG. 1, the system comprises at least one electrotactile feedback device 10 which, based on certain inputs 14, orders an interface or multi-pad electrode 13 (formed by small pads forming a matrix), located on a non-damaged body part of the user, to deliver low intensity bursts of electrical pulses. In other words, it delivers time and space distributed electrical stimulation. The electrotactile feedback device 10 also comprises a at least one electrical stimulator and multiplexing unit, not shown in FIG. 1, acting as a galvanically isolated pulse router capable of synchronously or asynchronously activating the discrete pads on the multi-pad electrode 13 in response to the instructions (electrical signals) received from a processing unit. As a consequence, the multi-pad electrode 13 applies a time and space distributed transcutaneous electrical stimulation through the user's skin. The bursts of pulses are sent via these small pads at different times, different frequencies and/or different intensities in order to generate distinctive signals that activate skin receptors and thereby afferent (somatosensory) neural systems and sensory cortex. The term "feedback" refers to the stimulation produced over multi-pad electrode 13 that provides information of interest regarding the system inputs 14 to the user.

The multi-pad electrode 13 of FIG. 1 can be placed on the stump of a subject's arm, in which case the non-illustrated artificial (prosthetic) body part is an artificial hand, or can be used with a non-amputated body part, for example with a body part with partial or complete loss of sensation.

Figure 2:
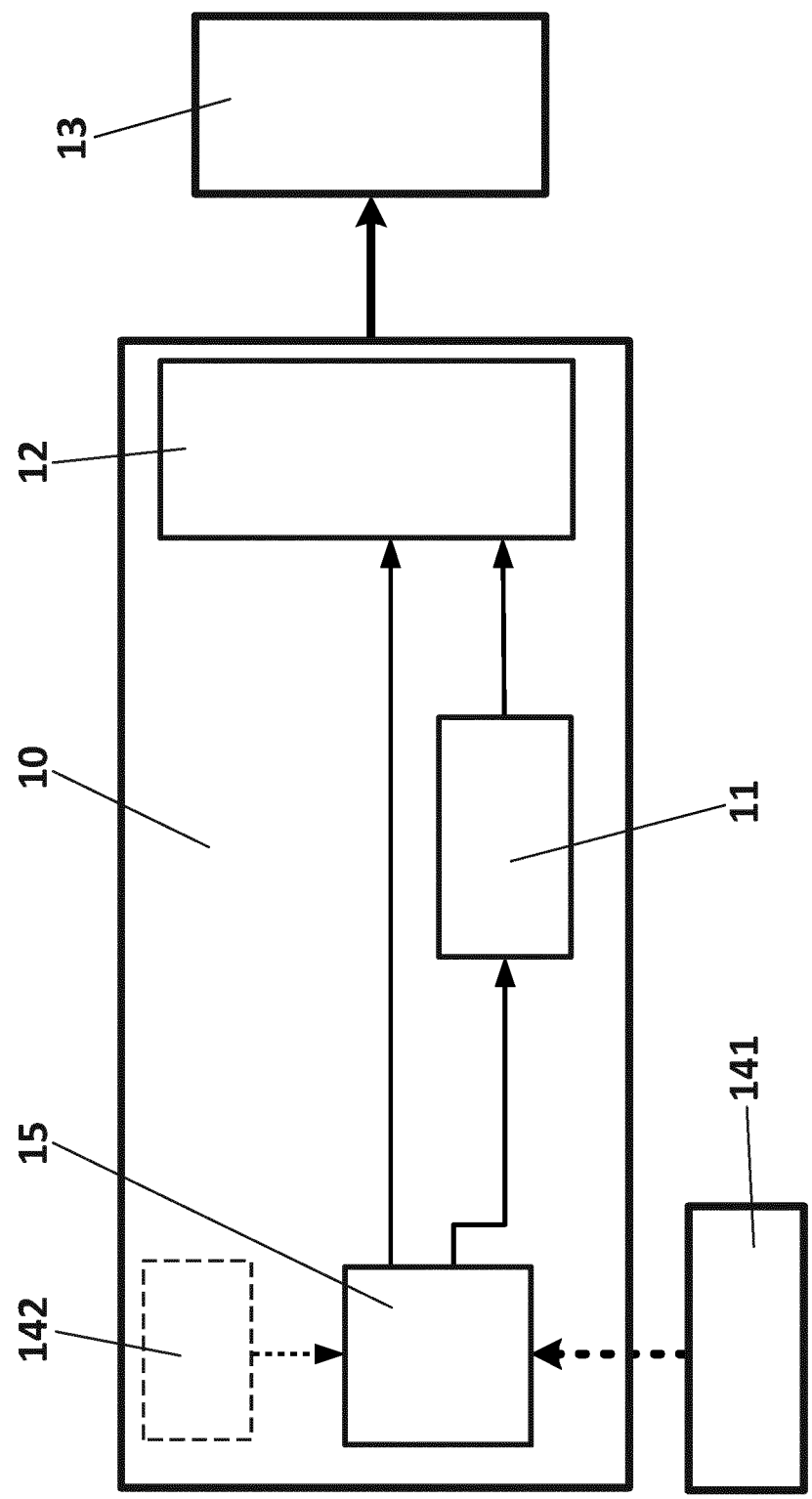
FIG. 2 illustrates a block diagram representing an electrotactile feedback interface according to an embodiment of the disclosure.

FIG. 2 shows a block diagram of the system outlined in FIG. 1. Two main blocks are represented: an electrotactile feedback device 10 and a multi-pad electrode 13. The device 10 has a processing unit or processing means 15 (which in the sketch of FIG. 1 is integrated in the device 10), which controls the stimulation parameters (i.e. active electrodes, stimulation frequency, pulse width and amplitude) to be delivered to the multi-pad electrode 13 based on a defined mapping scheme of one or more inputs 14. The processing unit 15 processes the input signals 14 and selects the adequate stimulation parameters as a response thereto, based on an intuitive mapping scheme explained later. The mapping scheme is defined in the processing unit 15. The device 10 also has a stimulation unit 11, also referred to as an electrical stimulator 11, which produces the electrical pulses of desired parameters (such as amplitude, duration and frequency) based on the demands of the processing unit 15. The device 10 also has a multiplexing unit 12, which conducts the electrical pulses from the stimulation unit 11 to the desired pad on the multi-pad electrode 13, based on the demands of the processing unit 15. The arrow that directly connects the processing unit 15 and the multiplexing unit 12 represents the mapping of the stimuli location, while the arrow that connects the processing unit 15 and the electrical stimulator 11 represents the mapping of the stimulation parameters. In other words, the processing unit defines the scheme of stimulation and the stimulator generates the pulses that are delivered to the specific location on the multipad electrode. The electrotactile interface is the feedback provided to the user through sensory stimulation. The processing unit calculates the stimulation pattern based on a predefined mapping scheme. The electrical stimulation unit produces the stimulation pulses and controls the electrical current applied to the skin of the user in order to comply with the processing unit demands. The multiplexing unit 12 routes the pulses to the desired location on the multipad electrode 13, based on the information from the processing unit.

The system inputs 14 can be external system inputs 141 and/or signals directly measured by a data acquisition unit 142 comprised in the electrotactile feedback device 10, as shown in FIG. 2. External inputs 141 include any sensory information from the artificial body part or sensory system for body extremity without sensation. These inputs can be gathered through an analog, digital or wireless communication interface. Inputs from the data acquisition unit 142 can include EMG, inertial measurements or measurements of any other physical property carried over by the data acquisition device itself. In a preferred embodiment, the data acquisition unit 142 is based on an EMG amplifier, thus capturing EMG input signals. Alternatively, the data acquisition unit 142 can be based on at least one inertial sensor.

These inputs 14 141 142, once processed, are transferred to the user in the form of cutaneous stimulation over the interface formed by the multi-pad electrode 13. The processing unit 15 of the electrotactile feedback device 10 defines intuitive mapping schemes for the input signals. The mapping schemes are designed to resemble the process that is happening with the artificial hand or body extremity without sensations. For instance, hand opening (departure of fingers) is mapped through the departure of the active electrodes. Increase of force is mapped through increase of stimulation frequency. This makes the mapping intuitive and easy to learn, as reported by the subjects who have participated in different tests and experiments with the inventive system. FIGS. 7 to 10 show some proposed sets of mapping schemes according to an embodiment of the disclosure.

In a particular embodiment, only one input signal 14 is required for providing the electrocatile feedback, and therefore, the data acquisition unit 142 is not a compulsory part of the system if there is one or more external system inputs 141 and vice versa: external inputs 141 are not required if there is one or more signals measured with the data acquisition unit 142 of the electrotactile feedback device 10. Alternatively, both type of input signals can be present.

In the particular embodiment in which the system is used by a person wearing an artificial body part (for example a hand prosthesis) or a sensory system (for example a data glove over the hand), the system inputs 14 may comprise sensory information obtained from the sensors comprised in the prosthetic device or sensory system. Non-limiting examples of conventional sensors comprised in prosthetic devices or sensory systems are touch sensors, pressure sensors, force sensors, bend sensors, vibration or inertial sensors, temperature sensors, moisture sensors, joint encoders or any combination thereof, or any other sensor capable of responding to a stimuli, and may be one sensor or a plurality of sensors or multisensors having the ability to sense different stimuli at the same time. These sensors comprised in an artificial body part (for example a hand prosthesis) or a sensory system (for example a data glove over the hand or a functional electrical stimulation (FES) hand grasp system or neuroprosthesis for hand grasp) are placed at places at which the sensory feedback is desired. All these inputs 14 are external inputs 141. If an artificial body part is used, the artificial body part (such as an artificial hand or FES hand grasp system) preferably comprises sensors and system inputs 14 that enable a closed loop control of the artificial hand. The system enables a feed-forward myoelectric control of the artificial body part or sensory system. It is based on multiple recordings from the muscles in the remaining parts of the body (stump), which can enable the user natural like control of the prostheses or sensory system based on the biofeedback from these control signals. This natural-like control is not possible in artificial body parts with no feedback, requiring the user to watch the artificial body part in order to control it. Inputs 14 can be sensory measurements from the artificial extremity or the sensory system for a body extremity without sensation and/or can be based on control signal measurements (e.g. EMG for the myoelectric prosthesis). If they contain measurements from sensors in the prosthesis or sensory system they can be used for closed loop control and if they are based on control signal they can be used for feed-forward control of an artificial extremity (such as a hand) or a sensory system (such as a data glove). EMG measurements can be taken by the data acquisition unit 142 or can be external inputs 141 from the prosthesis or from the sensory system. These signals are only of interest for feedback if the system is used for control of artificial body part or sensory system. A prosthetic device (or a sensory system) produces proprioceptive sensory information based on encoders that are built therein, as well as sensory information, e.g. force, measured thereby. For myoelectric prosthesis, the EMG signal measured by an EMG acquisition system through recording electrodes (after various filtering and processing) is the control signal that a user has to produce in order to control the prosthesis. Control signals can be determined by the prosthetic device or by a control interface (understood as any device that can obtain control signals if they are not obtained directly by the prosthesis). In the case of myoelectric control, the control signal is EMG, but it can be any other bio physiological signal that is used to drive the prosthesis). Control signals are acquired as external inputs 141 to the system or they can be calculated in the processing unit 15 based on the control signal measurements performed by the data acquisition unit 142 of the electrotactile feedback device 10. If control signal measurements are performed by the electrotactile feedback device 10, they can also later be forwarded to the control interface (or to the prosthesis or sensory system if the control interface is not incorporated in the prosthesis or sensory system). In the preferred embodiment, system inputs 14 include the control signal (feed-forward) for the aperture, flexion, rotation and grasping force of an artificial hand or hand with pour sensitivity. They may additionally include the sensory information (closed loop). In other words, information from the sensors in the prosthesis or sensory system implies closed loop control, while information about control signals (EMG or inertial measured by the prosthesis, sensory system or the electrotactile feedback itself) implies feed-forward control. Mapping of these input signals 14, is calculated by the processing unit 15 in order to provide the electrotactile interface.

The design of the information coding (pattern or mapping scheme), an implementation of which is shown in FIGS. 7-10, is based on the analysis of the distinctive stimulation patterns which can be clearly distinguished by the user. The inventors have observed in their studies that the most reliable sensation that healthy subjects and amputees could distinguish was the location of the stimuli and the frequency of stimulation. On the contrary, changes of pulse width and stimulation amplitude resulted with either insufficient recognition of stimuli or unpleasant stimulation. This is the main reason why in the system of the disclosure, the information is preferably coded in the stimuli location and the frequency of stimulation. The term "information" refers here to the sense of heat, cold, pressure, etc., to the force produced by a prosthesis or sensory system and/or to proprioceptive information (aperture, rotation, flexion), and/or to any other information from any other sensor in the prosthesis or data glove.

Next, two preferred embodiments of the system for transferring proprioceptive information from an artificial (prosthetic) body part or from a body part with partial or complete loss of sensation (via a sensory system) to the skin of the subject are described. In particular, the embodiments refer to an artificial (prosthetic) hand or to a hand with partial or complete loss of sensation (and therefore wearing a sensory system).

Figure 3:
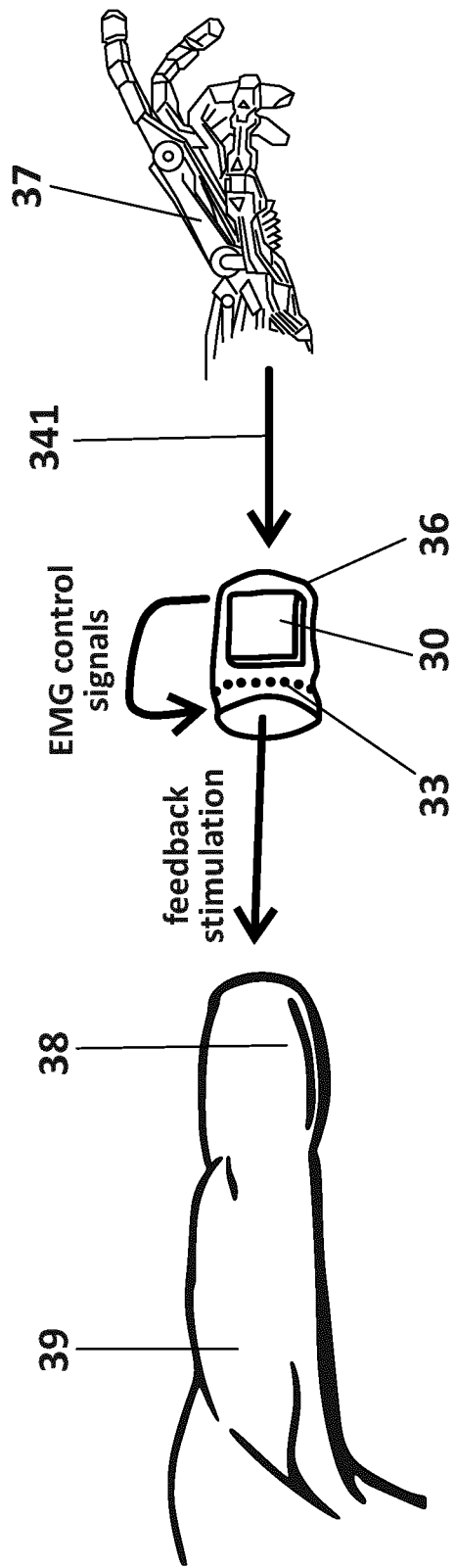
FIG. 3 shows an electrotactile feedback interface device for transferring proprioceptive and sensory information from an artificial hand incorporated in a socket.

In a preferred embodiment, shown in FIG. 3, the system having the electrotactile feedback device 30 and the multi-pad stimulation electrodes 33 is incorporated in a socket 36 of an extremity prosthesis (or artificial extremity) 37 and is therefore placed over the stump 38 of the user 39. In other words, FIG. 3 illustrates a socket 36 of an extremity prosthesis 37. The socket 36 comprises an electrotactile feedback device 30 and a multi-pad electrode 33. In this particular embodiment, the prosthesis is an artificial hand 37. In a particular embodiment, the multi-pad electrode 33 is embedded in the socket 36. Production processes and materials of the socket and electrodes are out of the scope of this disclosure. In FIG. 3, external input signals 341 are captured from the prosthesis 37, while the data acquisition unit (not illustrated in FIG. 3) comprised in the electrotactile feedback device 30 acquires control signals (EMG control signals, for instance). The arrow from device 30 to the multi-pad electrodes 33 in FIG. 3 is intended to emphasize that the control signals can be measured by the device itself and they are not coming from the artificial body part 37. Feedback stimulation is provided through the multi-pad electrode 33 to the stump 38.

Figure 4:
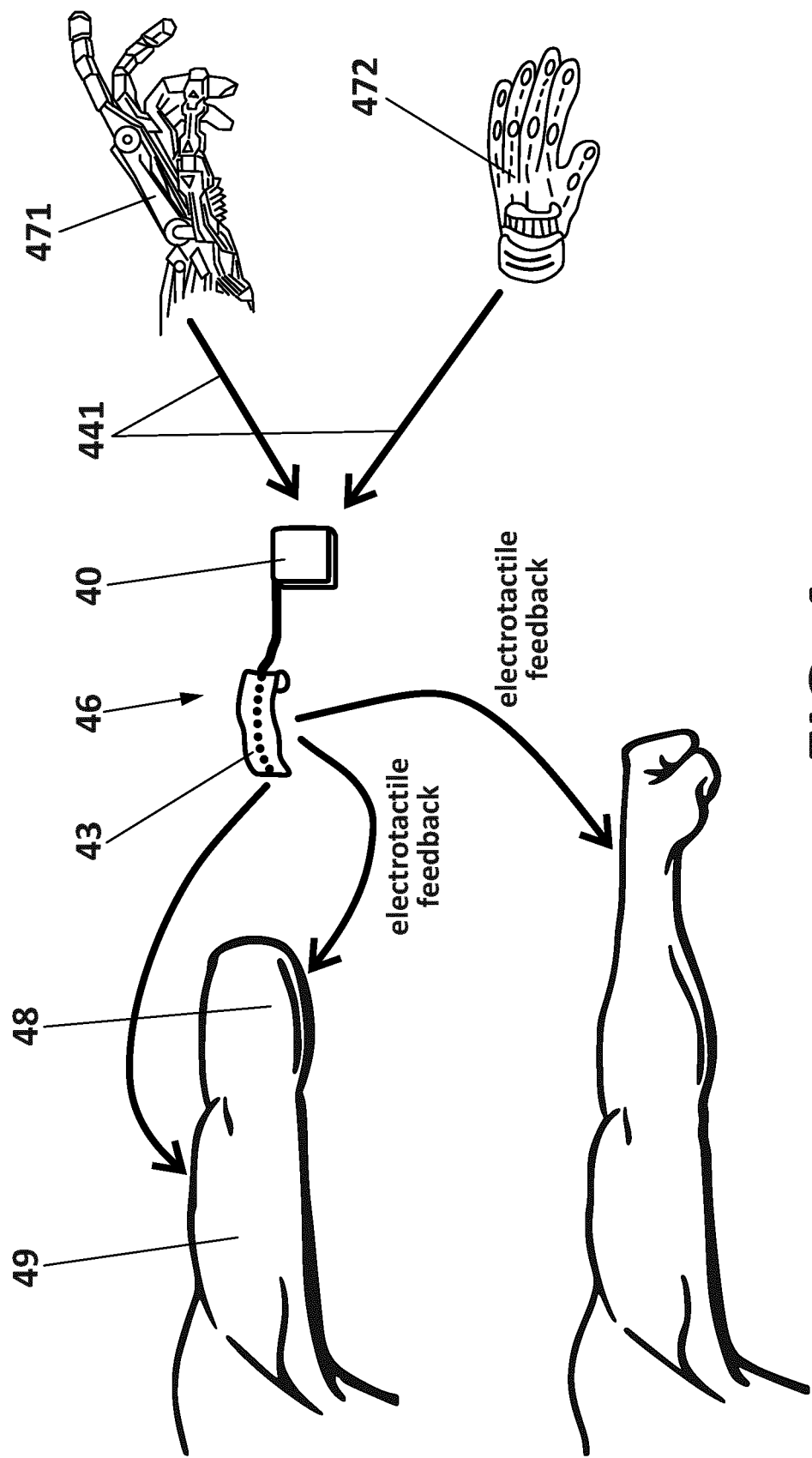
FIG. 4 shows an electrotactile feedback interface device for transferring proprioceptive and sensory information from an artificial hand placed in a garment that can be positioned over any part of the body.

In an alternative embodiment, FIG. 4 illustrates a garment 46 comprising a multi-pad electrode 43. In other words, the multi-pad stimulation electrodes 43 are integrated in a flexible garment 46 that can be positioned over any part of the body of the user 49, not necessarily the stump of the missing body part. The garment 46 can be used by a user wearing a prosthesis (top part of FIG. 4) or by a user having a body extremity without sensation (but not been amputated)

(bottom part of FIG. 4). The garment 46 can be placed on the stump 48 of the amputee 49 (if the system is used with a prosthesis 471) or on an arbitrary position on the arm (if the system is used with a prosthesis 471 or if the system is used with a sensory system 472 for the body part without sensation). The illustrated sensory system 472 is a data glove. In the first case (system used with a prosthesis), the multi-pad stimulation electrodes 43 and the electrotactile feedback device 40 can be used independently from the myoelectrical device and from the socket used to mount the artificial extremity 471 to the stump 48 of the subject 49. The electrotactile feedback device 40 can be either integrated in the same garment 46 or can be located somewhere else. The electrotactile feedback device 40 and the multi-pad electrode 43 must be physically connected. Therefore, in a preferred embodiment, they are in the same garment 46. In a particular embodiment, the glove 472 has feedback capabilities (capability for informing the user about proprioceptive control information). Typical examples of feedback capabilities of sensory systems 472 such as gloves are capability of measuring bending or capability of measuring angles defined by finger phalanxes. In addition, sensory systems 472 such as gloves provide sensory information, in particular touch or force capabilities. For example, when a user wearing such a glove grasps something, the glove provides proprioceptive information while the glove is being moved in order to grasp the object, and when the object is finally grasped, proprioceptive signals stop. Then touch or force information is provided. The proprioceptive information is sent to the user. Preferably, a combination of proprioceptive and sensory (touch) information is sent to the user through stimulation.

The electrotactile feedback device can be connected to an artificial hand (extremity) 37 471 or to a sensory system 472, such as a data glove. These connections can be analog/digital wired connections (as shown for example in FIG. 3) or wireless ones through any wireless communication interface known to the state of the art. In the embodiment of FIG. 4, such communication is preferably wireless.

The multi-pad electrode 13 33 43 can be manufactured using the materials and technology known to the state of the art, such as conductive silicon rubber inserts, screen printing of conductive inks, where contact with the skin is established either through direct contact with dry electrode surface or via a conductive hydrogel material insert between the skin and the electrode. The pads or electrodes which form the multi-pad electrode 13 33 43 are small enough to allow controlled current flow between the anode and cathode. In the preferred embodiment the location of the cathode on the body determines the activated skin receptors and the anode can be located at any position of the same body. Thus, a pad on the multi-pad electrode 13 33 43 used as cathode will determine the location of the recognized stimuli. Thanks to this configuration, mapping of the input signals 14 through this electrotactile interface having the multi-pad electrodes 13 33 43 is possible by selecting/changing the stimuli location (that is to say, by selectively activating/deactivating individual pads) and/or by controlling the stimulation parameters (frequency, pulse width or amplitude of stimulation).

The multi-pad electrode 13 33 43 is preferably designed to be located on a non-damaged body part of the user in such a way that the electrodes or pads which form the multi-pad electrode 13 33 43 are circularly positioned on or over said body part. In the event that the user has a prosthesis coupled to a stump, this body part is preferably the stump of an arm (or leg) of the user. The size and shape of the pads are chosen so as to produce comfortable but also selective stimulation.

Figure 5:
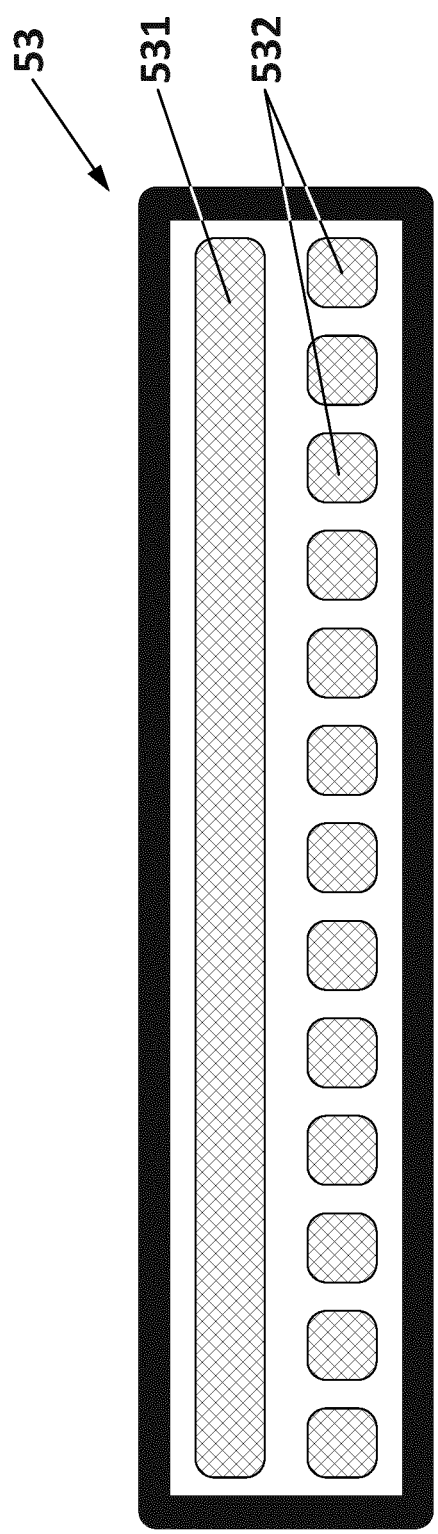
FIG. 5 shows a possible implementation of a multi-pad electrode for an electrotactile feedback interface, having a common anode.
Figure 6:
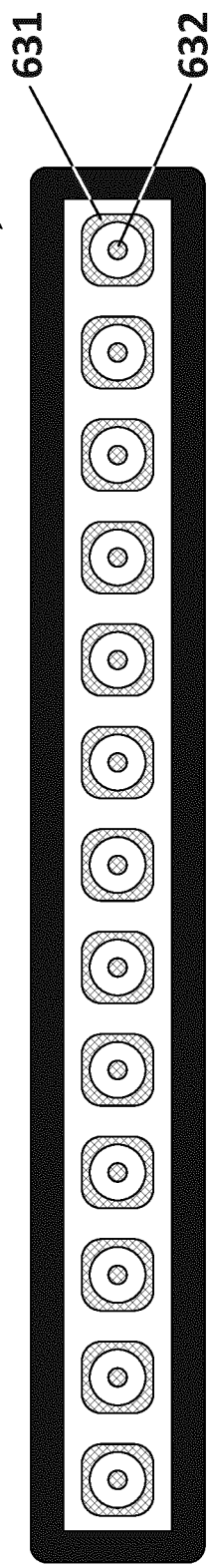
FIG. 6 shows an alternative implementation of a multi-pad electrode for an electrotactile feedback interface, having concentric pads.

The layer with multi-pad electrodes is preferably integrated into a soft and flexible substrate that is designed in a manner which allows positioning of the system over any part of the body extremity; thereby facilitating the application of the system. Two preferred multi-pad electrode designs are shown in FIGS. 5 and 6, but other shapes and number of pads could alternatively be utilized. The multi-pad electrodes can be produced to enable a dry skin interface (e.g. conductive rubber) designed in a manner which allows positioning of the system in a socket of an artificial limb. The electrodes can also be integrated into a soft and flexible substrate that is designed in a manner of a garment which allows positioning of the system over an individually selected position on a body. FIG. 5 shows a possible implementation of a multi-pad electrode 53, comprising a common anode 531 and a plurality of cathodes 532. The multi-pad electrode 53 takes the form of a band, belt or tape configured to surround the stump. The cathodes 532 are disposed along the band, forming a line of electrodes, while the anode 531 preferably takes the form of a long electrode parallel to the list of cathodes 532. FIG. 6 shows an alternative implementation of a multi-pad electrode 63 comprising a plurality of pairs anode 631—cathode 632, wherein each cathode 632 is surrounded by one preferably concentric anode 631. The multi-pad electrode 63 also takes the form of a band, belt or tape configured to surround the stump. The pairs anode-cathode are disposed along the band, forming a line of pads or electrodes.

Next, it is described how the proprioceptive and sensory information from the artificial body part (or body part with partial or complete loss of sensation) is coded and how the stimulation parameters (pulse width, stimulation amplitude and frequency of stimulation) are modified in order to correctly respond to several system inputs. In particular, four exemplary messages are illustrated on FIGS. 7-10. These are non-limiting examples, since additional messages can be used.

In a preferred embodiment, the system is able to react to four independent inputs 14 obtained from an artificial hand or a sensory system for a hand with poor sensitivity. The four different input signals are: the aperture of an artificial hand (from closed grasp to open hand); the force measured by the artificial hand or sensory system; the rotation of the artificial hand or sensory system; and the flexion/extension of the artificial hand or sensory system. The system of the disclosure reacts to these four independent inputs by defining (at the processing unit 15) four respective stimulation coding schemes which can be used to transfer information of interest to the user. Depending on the artificial hand or sensory system, if used, these inputs can include, for instance, the artificial hand proprioceptive information about aperture, rotation and the flexion/extension of the artificial hand or glove, as well as the information from the eventual sensors built into the artificial hand or glove (touch, force, vibration, temperature, moisture sensors or others).

Figure 7:
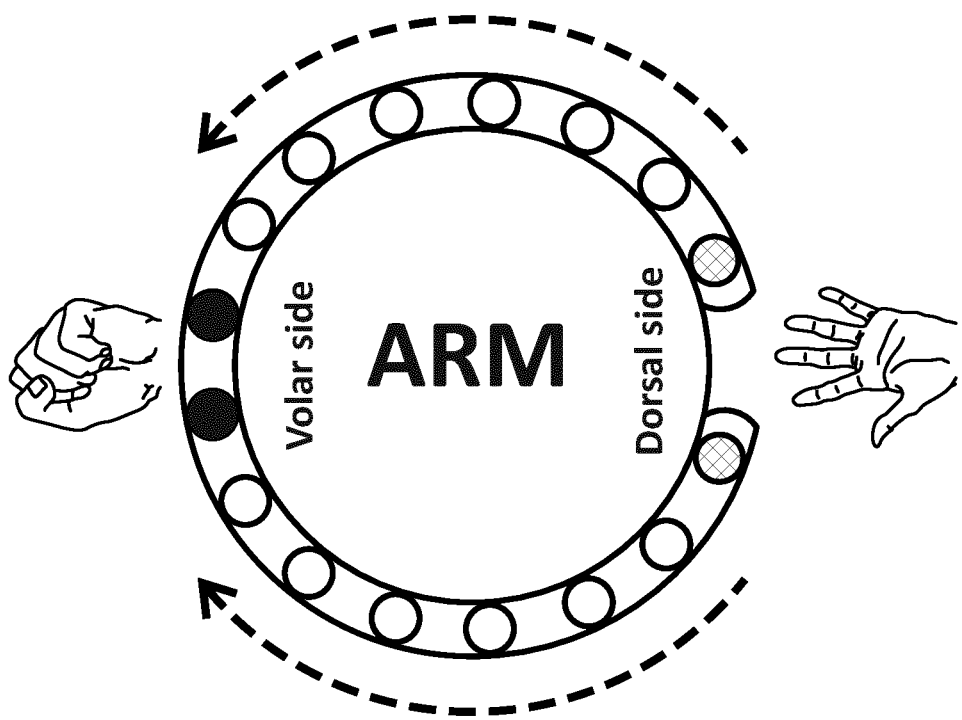
FIGS. 7 to 10 show different mapping/coding schemes for the active electrodes for different input signals.

FIG. 7 represents the proposed coding/mapping scheme preferably selected to react to the input signal associated to the aperture of the artificial hand or glove. In this scheme, the pads or electrodes to be activated when the artificial hand or glove is fully open are the two ones disposed at the central dorsal part of the arm. When the hand starts to close these pads are deactivated and adjacent pads are activated. This process is continued until the pads or electrodes disposed at the central volar part of the arm are activated, which represents closed hand. The dotted arrows in FIG. 7 describe the evolution of the activation/deactivation of pads. Alternatively, the activation can be the other way round, that is to say, the first pads to be activated are the two ones disposed at the central volar part of the arm, the process ending with the activation of the two pads disposed at the central dorsal part of the arm. In other words, the active pads change from a first situation in which either the two end pads are active and the remaining ones are not until only the two central pads are active; or vice versa. The multi-pad electrode needs to be of a shape that permits such ordered activation/deactivation of pads and needs to be disposed around the arm or arm stump. An exemplary appropriate shape of the multi-pad electrode is a bracelet.

Figure 8:
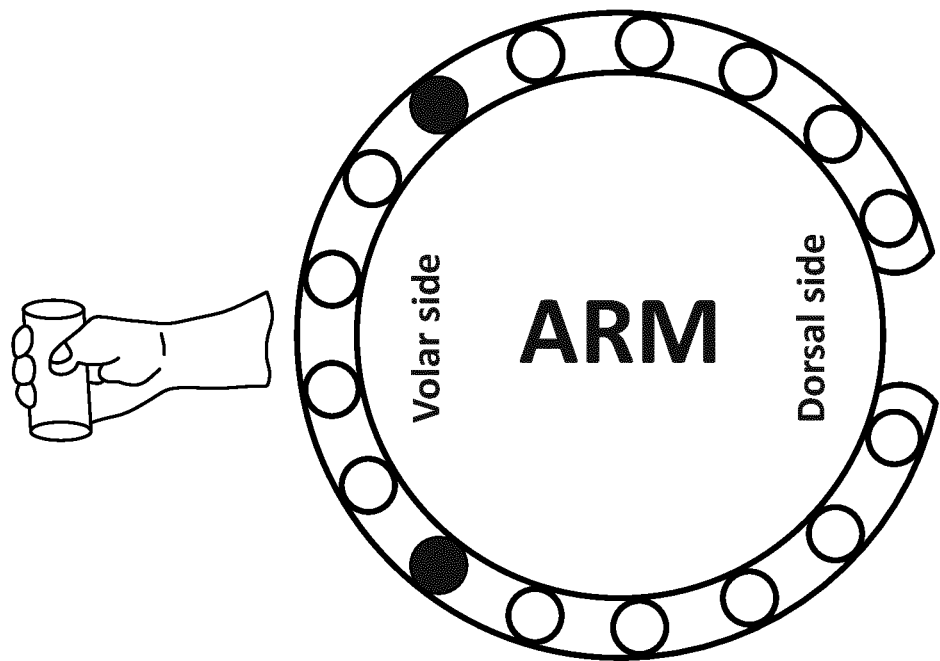

FIG. 8 represents the proposed coding/mapping scheme preferably selected to react to the input signal associated to the force measured by the artificial hand or glove. In this case, the mapping is done by changing the stimulation frequency on the one or more active electrodes in response to changes in force. For example, an increase in the force measured by the artificial hand or glove is translated into an increase in the stimulation frequency. In other words, increase of the force applied by the artificial hand (or eventually sensing system) is coded with the increase of stimulation frequency on the active electrodes. The illustrated mapping in FIG. 8 is not limited to two of active electrodes (in dark in FIG. 8). In the preferred embodiment, the distance between these two active pads codes the aperture, as explained in relation to FIG. 7. This means that, if for example the user is grasping an object thicker than the one shown in FIG. 8, the active electrodes (which in this embodiment have been selected to be two, but could be a different amount of electrodes) are not the dark ones in FIG. 8, but other electrodes closer to the dorsal side. If, on the contrary, the user is for example grasping a straw—an object thinner than the one shown in FIG. 8—, the active electrodes are not the dark ones in FIG. 8, but other electrodes closer to the volar side. It is important to point out that the coding scheme for the force measured by the artificial hand in combination with the previously described coding scheme for aperture of the artificial hand or glove can provide the user with information about the stiffness of the object that is being grasped.

For instance, the user will be able to recognize if the object is being squeezed by the artificial hand or glove if, when the force is increasing, the aperture is decreasing. This is possible due to the proposed coding of the aperture/grasping and the applied force with respective independent stimulation parameters (stimuli location and stimulation frequency).

Figure 9:
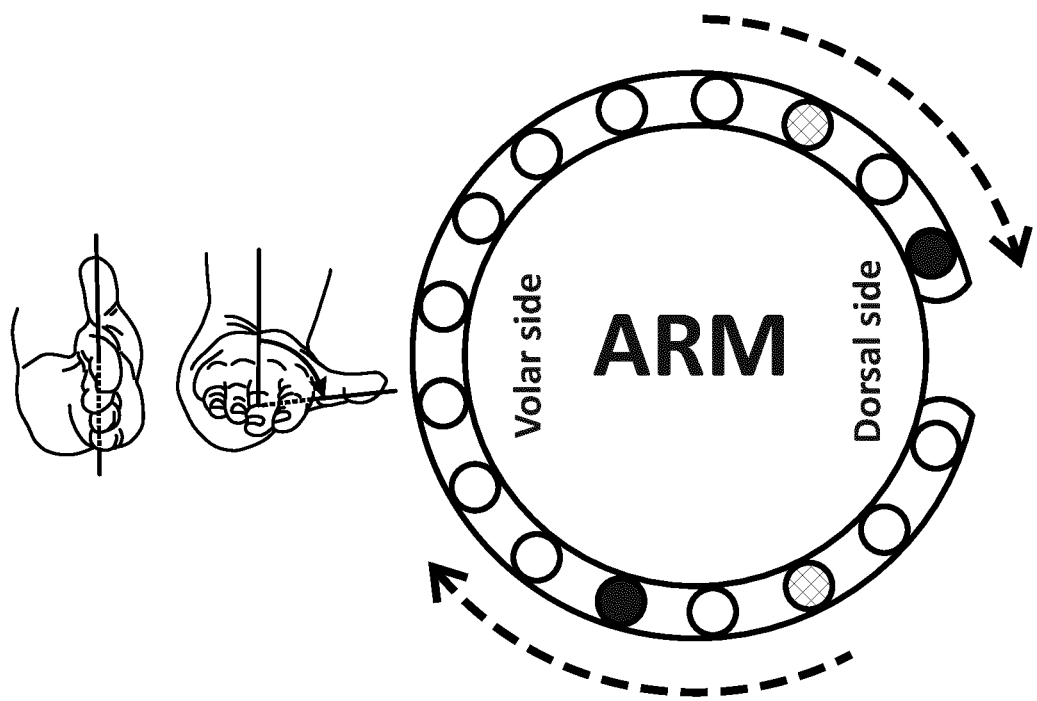

FIG. 9 represents the proposed coding/mapping scheme preferably selected to react to the input signal associated to the rotation of the artificial hand or glove. A rotation of the artificial hand or glove is translated (coded) into a rotational evolution of the active pads on the circularly positioned multi-pad electrode. The first pad to be activated corresponds to the original position of the artificial hand or glove (at the instant of starting the rotation). During the rotation of the artificial hand or glove, the already active pad is deactivated while the following pad in the direction of the rotation is activated, and so on, until the pad corresponding to the end of the rotation is activated. In the proposed solution this information coding is independent from the described coding schemes represented on FIGS. 7 and 8, and can therefore, be used coupled with the information about the hand aperture and applied force. In other words, the proposed coding schemes actually enable the user to detect for example rotation and aperture/grasping simultaneously, or rotation and applied force simultaneously.

Figure 10:
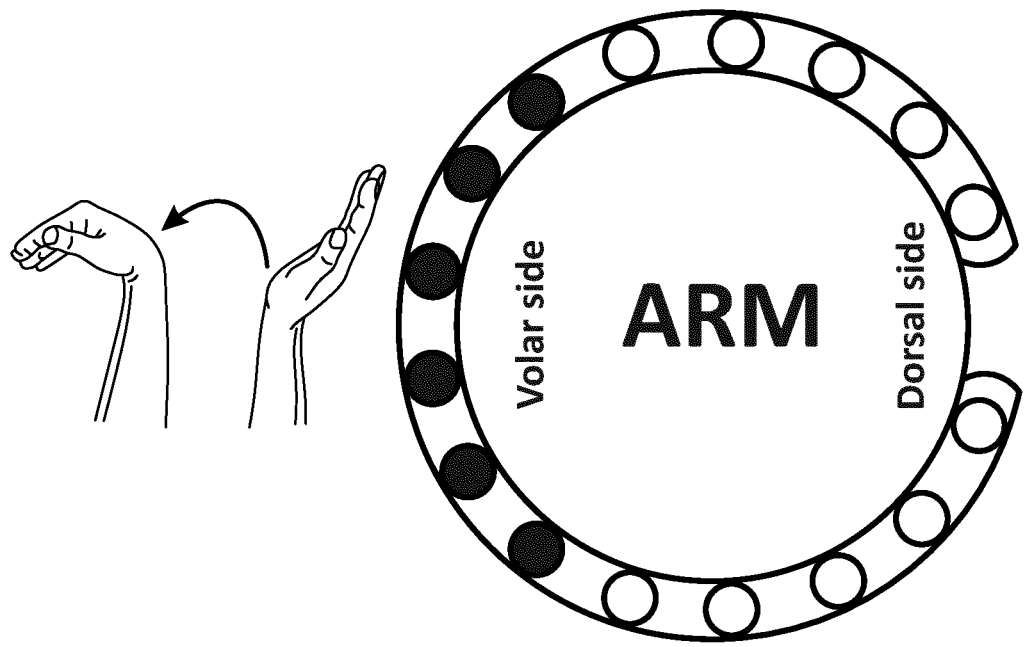

FIG. 10 represents the proposed coding/mapping scheme preferably selected to react to the input signal associated to the flexion/extension of the artificial hand or glove. The flexion/extension of the artificial hand or glove is translated (mapped) into the activation of additional pads on the multi-pad electrode in the preprogrammed time sequence. This message or coding scheme is different from the three previous ones because, unlike those ones, this is intended to send relative information. Only when the angle of the artificial hand (or glove or FES hand grasp system) with respect to the corresponding arm changes by some amount (for instance 15 degrees), several electrodes (for instance—but not limitedly—6) on the same side of the arm/stump are activated instead of a different amount of electrodes (for example 2) that are active otherwise. The coding scheme associated to the flexion/extension of the artificial hand or system can be combined with the force scheme since the stimulation frequency can be perceived independently from localization or number of activated pads when at least one pad is stimulated.

In sum, since the four coding schemes are independent from each other, more than one of them can be used simultaneously for enabling the user to react to two or more independent inputs. In other words, the system is capable of combining at least two functions. As a matter of example, it is for example possible to use the position of 2 afferent stimulation pads to encode the aperture of the hand and provide with a frequency coding the force information (e.g. higher stimulation frequency for higher force). Also for example, it is possible to combine hand rotation (pro/supination) and grasp force (frequency) is described. This is possible because stimulation position (also referred to as stimuli location) and stimulation frequency are independent variables and therefore can be used to encode simultaneous afferent signals (for example, aperture/grasping is encoded with stimuli location and force is encoded with frequency). In sum, the proposed coding schemes actually enable the user to notice if, for instance, an object is being squeezed (noticed thanks to the simultaneous increase of stimulation frequency (that represents force increase)) and the proximity of the active electrodes (that represents decrease of aperture).

As can be observed, in the illustrated embodiments corresponding to four coding schemes, the physical structure of the electrode must be circular (bracelet type) around the body part on which it is placed. The illustrated combination of messages can only be used in this configuration of the electrode.

In summary, in this exemplary embodiment, wherein a person is wearing an artificial hand or glove and the inventive system having a bracelet-type multi-pad electrode (FIG. 5 or 6) has been disposed on his/her arm stump, mapping is done as following: movement of the active electrodes from the central dorsal part of the arm towards the central volar part of the arm is based on the changes of the hand aperture (FIG. 7), changes of the stimulation frequency on the active electrodes is based on the grasping force (FIG. 8), rotation of active electrodes is based on rotation of the artificial hand or glove (FIG. 9) and the change in the number of active electrodes is based on flexion/extension of the artificial hand or glove (FIG. 10). One of the advantages of the proposed interface is the concurrent transfer of the hand aperture and force information that enables the user to feel if the grasped object is being squeezed by the force applied. The system is of course not limited to this particular coding scheme, and different proprioceptive and sensory information and coding schemes can be used for transferring information over these four independent circularly positioned multi-pad electrode parameters. The multi-pad electrode works similarly and the information is similarly coded in the person, who instead of wearing an artificial hand, is wearing a sensing glove on a hand with poor sensitivity.

Prior to the routine use of the system of the disclosure, the user (for example, amputee) needs to undergo short training, in order to learn the correlation between what is sensed (for example by the sensors in the prosthetic body part) and the real feeling produced on the skin by the multi-pad electrode. Once this training is fulfilled, the person is ready to autonomously use the inventive system.

As apparent from the content of this description, the proposed system and method can directly improve the functioning of the artificial prosthesis, such as hands, since it enables the user to feel it as a part of the body. In this way, the amputee is able to effectively use the artificial hand and have a better quality of life. This electrotactile feedback device can be used to improve the performance of existing commercially available myoelectric prostheses, and to increase the level of their acceptance by direct increase of cost-benefit ratio. Average rejection rate of myoelectric prostheses today is more than 25%, both, in young and adults, which is mainly associated with lack of functional need, discomfort (excessive weight and heat) and impediment to sensory feedback. For example, amputees often choose a conventional (functionally limited) cable driven prosthesis instead of effortlessly controlled, more sophisticated myoelectric hands, simply because the former provides a restricted feedback through the cables (so called extended physiological proprioception).

Based on the known ability of the cortex to self-adapt (learn), the user will develop a new modality of exteroception and proprioception. The pads that are made active will follow the signals coming from the sensors built into the artificial hand (touch, force, vibration, temperature, moisture, joint encoders, etc.), other sensory systems (e.g. data glove over the hand) or directly from the EMG measurements that are used to control the myoelectric artificial hand.

On the other hand, the disclosure is obviously not limited to the specific embodiment(s) described herein, but also encompasses any variations that may be considered by any person skilled in the art (for example, as regards the choice of materials, dimensions, components, configuration, etc.), within the general scope of the disclosure.

The invention claimed is:

1. A system for transferring proprioceptive information from a prosthesis or a sensory system configured to be disposed at a body part having poor or no sensation, to the skin of a user wearing the prosthesis or the sensory system, wherein said prosthesis is an artificial hand or said body part having poor or no sensation at which the sensory system is configured to be disposed is a hand, the system for transferring proprioceptive information comprises:
 a device for providing electrotactile feedback in the form of a stimulation pattern defined from at least one input signal; and
 at least one multi-pad electrode configured to be positioned on an upper limb part of the body of said user, circularly surrounding the stump or body part of the user, said multi-pad electrode comprising a plurality of pads configured to be selectively and discretely activated or deactivated according to said stimulation pattern, wherein the plurality of pads comprised in said at least one multi-pad electrode are disposed in single array along the multi-pad electrode;
 said device comprises:
 a processing unit for processing said at least one input signal, wherein said at least one input signal has information about an opening, a flexion, a rotation and/or a grasping force of said prosthesis or from said sensory system, and based on said at least one input signal said processing unit is configured to determine one of a plurality of stimulation patterns comprised in a predefined mapping scheme, representing a corresponding plurality of operational parameters of said artificial prosthesis or sensory system;
 an electrical stimulator for producing a plurality of electrical pulses based on said selected stimulation pattern;
 and a multiplexing unit for conducting said electrical pulses from said electrical stimulator to said at least one multi-pad electrode, selectively activating or deactivating the discrete pads of said multi-pad electrode and changing the configuration parameters of the discrete pads based on said stimulation pattern comprised in said predefined mapping scheme, such that time and space distributed cutaneous stimulation corresponding to said at least one input signal is enabled,
 wherein said at least one input signal controls the opening of a prosthesis or of a sensory system configured to be disposed at an upper limb having poor or no sensation, wherein the opening of the artificial hand or of the sensory system is configured as follows:
 in an initial position in which the hand is open, two of the plurality of pads configured to be disposed at a furthermost dorsal part of the arm are activated, and when the hand starts closing the two pads are deactivated while adjacent pads of the plurality of pads are activated, this process being continued until the hand is closed and pads of the plurality of pads configured to be disposed at a central volar part of the arm are activated;
 or in an initial position in which the hand is open, two of the plurality of pads configured to be disposed at a central volar part of the arm are activated, and when the hand starts closing the two pads are deactivated while adjacent pads of the plurality of pads are activated, this process being continued until the hand is closed and pads of the plurality of pads configured to be disposed at a furthermost dorsal part of the arm are activated.

2. The system of claim 1, wherein said device further comprises a data acquisition unit configured to capture a control signal to be provided to said processing unit.

3. The system of claim 1, wherein said at least one input further comprises sensory information.

4. The system of claim 1, wherein said stimulation pattern is defined by at least one of the following stimulation parameters: location of the pad in the multi-pad electrode, stimulation frequency, stimulation pulse width, and stimulation pulse amplitude.

5. The system of claim 1, wherein said stimulation pattern is defined by the following stimulation parameters: stimuli location and frequency of stimulation.

6. The system of claim 1 further configured for transferring sensory information from said prosthesis or from said sensory system configured to be disposed at an upper limb having poor or no sensation, to the skin of a user wearing the prosthesis or the sensory system.

7. The system of claim 1, wherein said at least one input signal controls the grasping force of the prosthesis or of the sensory system configured to be disposed at an upper limb having poor or no sensation, wherein the grasping force applied by the artificial hand or measured by the sensory system has an associated coding scheme on the processing unit, in which the stimulation frequency on the one or more active pads is changed in response to changes in measured force.

8. A socket configured to be placed at one end on a stump of an upper limb and to receive an artificial extremity prosthesis at the opposite end, the socket comprising the system of claim 1.

9. A garment configured to be positioned either on an upper limb of a user having an artificial hand prosthesis or on a body part of a user having a sensory system at a hand without sensation, the garment comprising the system of claim 1.

10. A system for transferring proprioceptive information from a prosthesis or a sensory system configured to be disposed at a body part having poor or no sensation, to the skin of a user wearing the prosthesis or the sensory system, wherein said prosthesis is an artificial hand or said body part having poor or no sensation at which the sensory system is configured to be disposed is a hand, the system for transferring proprioceptive information comprises:
- a device for providing electrotactile feedback in the form of a stimulation pattern defined from at least one input signal; and
- at least one multi-pad electrode configured to be positioned on an upper limb of said user, circularly surrounding the stump or body part of the user, said multi-pad electrode comprising a plurality of pads configured to be selectively and discretely activated or deactivated according to said stimulation pattern, wherein the plurality of pads comprised in said at least one multi-pad electrode are disposed in single array along the multi-pad electrode;
- said device comprises:
- a processing unit for processing said at least one input signal, wherein said at least one input signal has information about an opening, a flexion, a rotation and/or a grasping force of said prosthesis or from said sensory system, and based on said at least one input signal said processing unit is configured to determine one of a plurality of stimulation patterns comprised in a predefined mapping scheme, representing a corresponding plurality of operational parameters of said artificial prosthesis or sensory system;
- an electrical stimulator for producing a plurality of electrical pulses based on said selected stimulation pattern;
- and a multiplexing unit for conducting said electrical pulses from said electrical stimulator to said at least one multi-pad electrode, selectively activating or deactivating the discrete pads of said multi-pad electrode and changing the configuration parameters of said discrete pads based on said stimulation pattern comprised in said predefined mapping scheme, such that time and space distributed cutaneous stimulation corresponding to said at least one input signal is enabled,
- wherein said at least one input signal controls the flexion or extension of a prosthesis or of a sensory system configured to be disposed at an upper limb having poor or no sensation, wherein when the flexion or extension of the artificial hand or of the sensory system is detected by the processing unit, the processing unit is configured to activate at least one additional pad on the multi-pad electrode in a preprogrammed time sequence.

11. The system of claim 10, wherein said at least one input further comprises sensory information and wherein the system is further configured for transferring sensory information from said prosthesis or from said sensory system configured to be disposed at an upper limb having poor or no sensation, to the skin of a user wearing the prosthesis or the sensory system.

12. The system of claim 10, wherein said stimulation pattern is defined by at least one of the following stimulation parameters: location of the pad in the multi-pad electrode, stimulation frequency, stimulation pulse width, and stimulation pulse amplitude.

13. The system of claim 10, wherein said at least one input signal additionally controls the grasping force of the prosthesis or of the sensory system configured to be disposed at an upper limb having poor or no sensation, wherein when the grasping force applied by the artificial hand or measured by the sensory system is detected by the processing unit, the processing unit is configured to change the stimulation frequency of the one or more activated pads in response to changes in measured force.

14. A socket configured to be placed at one end on a stump of an upper limb and to receive an artificial extremity prosthesis at the opposite end, the socket comprising the system of claim 10.

15. A garment configured to be positioned either on an upper limb of a user having an artificial hand prosthesis or on a body part of a user having a sensory system at a hand without sensation, the garment comprising the system of claim 10.

16. A system for transferring proprioceptive information from a prosthesis or a sensory system configured to be disposed at a body part having poor or no sensation, to the skin of a user wearing the prosthesis or the sensory system, wherein said prosthesis is an artificial hand or said body part having poor or no sensation at which the sensory system is configured to be disposed is a hand, the system for transferring proprioceptive information comprises:
- a device for providing electrotactile feedback in the form of a stimulation pattern defined from at least one input signal; and
- at least one multi-pad electrode configured to be positioned on an upper limb of said user, circularly surrounding the stump or body part of the user, said multi-pad electrode comprising a plurality of pads configured to be selectively and discretely activated or deactivated according to said stimulation pattern, wherein the plurality of pads comprised in said at least one multi-pad electrode are disposed in single array along the multi-pad electrode;
- said device comprises:
- a processing unit for processing said at least one input signal, wherein said at least one input signal has information about an opening, a flexion, a rotation and/or a grasping force of said prosthesis or from said sensory system, and based on said at least one input signal, the processing unit is configured to determine one of a plurality of stimulation patterns comprised in a predefined mapping scheme, representing a corresponding plurality of operational parameters of said artificial prosthesis or sensory system;
- an electrical stimulator for producing a plurality of electrical pulses based on said selected stimulation pattern;
- and a multiplexing unit for conducting said electrical pulses from said electrical stimulator to said at least one multi-pad electrode, selectively activating or deactivating the discrete pads of said multi-pad electrode and changing the configuration parameters of said discrete pads based on said stimulation pattern comprised in said predefined mapping scheme, such that time and space distributed cutaneous stimulation corresponding to said at least one input signal is enabled, wherein said at least one input signal controls the rotation of a prosthesis or of a sensory system configured to be disposed at an upper limb having poor or no sensation, wherein when the rotation of the artificial hand or of the sensory system is detected by the processing unit, the processing unit is configured to activate a first of the pads corresponding to an original position of the artificial hand or sensory system at the instant of starting the rotation, wherein during the rotation of the artificial hand or sensory system, the already activated pad is deactivated while the following pad in the direction of the rotation is activated, until the pad corresponding to an end of the rotation is activated.

17. The system of claim 16, wherein said at least one input further comprises sensory information, and the system is further configured for transferring sensory information from said prosthesis or from said sensory system configured to be disposed at an upper limb having poor or no sensation, to the skin of a user wearing the prosthesis or the sensory system, and wherein said stimulation pattern is defined by at least one of the following stimulation parameters: location of the pad in the multi-pad electrode, stimulation frequency, stimulation pulse width, and stimulation pulse amplitude.

18. The system of claim 16, wherein said at least one input signal additionally controls the grasping force of the prosthesis or of the sensory system configured to be disposed at an upper limb having poor or no sensation, wherein when the grasping force applied by the artificial hand or measured by the sensory system is detected by the processing unit, the processing unit changes the stimulation frequency on the one or more active pads in response to changes in measured force.

19. A socket configured to be placed at one end on a stump of an upper limb and to receive an artificial extremity prosthesis at the opposite end, the socket comprising the system of claim 16.

20. A garment configured to be positioned either on an upper limb of a user having an artificial hand prosthesis or on a body part of a user having a sensory system at a hand without sensation, the garment comprising the system of claim 16.

* * * * *